United States Patent
Song

(10) Patent No.: US 10,238,360 B2
(45) Date of Patent: Mar. 26, 2019

(54) AIR CALIBRATION

(71) Applicant: SHENYANG NEUSOFT MEDICAL SYSTEMS CO., LTD., Shenyang (CN)

(72) Inventor: Qinghe Song, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 206 days.

(21) Appl. No.: 15/206,096

(22) Filed: Jul. 8, 2016

(65) Prior Publication Data

US 2017/0042498 A1  Feb. 16, 2017

(30) Foreign Application Priority Data

Aug. 12, 2015 (CN) .......................... 2015 1 0498049

(51) Int. Cl.
*A61B 6/00* (2006.01)
*A61B 6/03* (2006.01)

(52) U.S. Cl.
CPC .............. *A61B 6/582* (2013.01); *A61B 6/032* (2013.01); *A61B 6/5205* (2013.01)

(58) Field of Classification Search
CPC ................................ A61B 6/032; A61B 6/582
See application file for complete search history.

(56) References Cited

U.S. PATENT DOCUMENTS

| | | | |
|---|---|---|---|
| 2005/0088177 A1 | 4/2005 | Schreck et al. | |
| 2011/0274240 A1 | 11/2011 | Sugaya et al. | |
| 2013/0156163 A1 | 6/2013 | Liu et al. | |
| 2014/0187910 A1 | 7/2014 | Culver et al. | |
| 2015/0030226 A1 | 1/2015 | Ihara | |
| 2016/0113617 A1* | 4/2016 | Herrmann ................ | A61B 6/42 378/207 |

FOREIGN PATENT DOCUMENTS

| | | |
|---|---|---|
| CN | 1657011 A | 8/2005 |
| CN | 101756707 A | 6/2010 |
| CN | 102376097 A | 3/2012 |
| CN | 103494612 A | 1/2014 |
| CN | 103519813 A | 1/2014 |
| CN | 103596502 A | 2/2014 |
| CN | 103845073 A | 6/2014 |
| CN | 103961125 | 8/2014 |
| CN | 104077758 A | 10/2014 |
| JP | 7327979 | 12/1995 |
| JP | 2001070297 A | 3/2001 |
| JP | 2008023039 A | 2/2008 |
| JP | 2011139786 | 7/2011 |
| WO | 2009096361 A1 | 8/2009 |
| WO | 2014077394 A1 | 5/2014 |

* cited by examiner

*Primary Examiner* — Dani Fox

(74) *Attorney, Agent, or Firm* — McCoy Russell LLP

(57) ABSTRACT

In an example, a method for air calibration is provided. An initial scanning condition may be generated from a subject scanning sequence of medical equipment, wherein, the subject scanning sequence is generated when a subject is scanned by the medical equipment to obtain an image of the subject and recorded in association with a subject ID uniquely identifying the subject. An air calibration scanning condition may be obtained by correcting the initial scanning condition. An air calibration may be performed on the medical equipment according to the air calibration scanning condition to generate air calibration data.

13 Claims, 4 Drawing Sheets

AIR CALIBRATION

CROSS-REFERENCE TO RELATED APPLICATIONS

The present application claims priority to Chinese Patent Application No. 201510498049.9, filed on Aug. 12, 2015, the entire contents of which are hereby incorporated by reference for all purposes.

BACKGROUND

The present disclosure relates to air calibration of medical equipment.

For medical-imaging-type medical equipment, e.g., CT (Computed Tomography) equipment and PET-CT (Positron Emission Tomography-Computed Tomography) equipment, a regular air calibration is usually required in order to remove ring artifacts or band-like artifacts generated in the obtained scan images when the medical equipment is scanning a subject. Before performing the air calibration, scanning parameters of the medical equipment for performing the air calibration procedure may be determined. A desired air calibration scanning condition may be selected according to the determined scanning parameters, and the air calibration may be performed based on each air calibration scanning condition. For medical equipment, a high-pressure bulb tube of the medical equipment may be exposed every time when performing the air calibration.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, Ultrasound, Positron Emission Tomography (PET), Linear Accelerator (LINAC), and biochemistry analyser. Currently, NMS' products are exported to over 60 countries and regions around the globe, serving more than 5,000 renowned customers. NMS' latest successful developments, such as 128 Multi-Slice CT Scanner System, Superconducting MRI, LINAC, and PET products, have led China to become a global high-end medical equipment producer. As an integrated supplier with extensive experience in large medical equipment, NMS is committed to the study of avoiding secondary potential harm caused by excessive X-ray irradiation to the subject during the CT scanning process.

BRIEF DESCRIPTION OF DRAWINGS

Features of the present disclosure are illustrated by way of example and are not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures may not be described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The example methods for air calibration of the present disclosure may be applied in various types of medical equipment for acquiring subject images through a scanning method, wherein the medical equipment may include CT equipment and PET-CT equipment, etc. Take CT equipment as an example; the CT equipment may scan a subject, such as a layer with a certain thickness of a certain portion of the subject, to obtain CT scan images by using X-ray beams. The core device of the CT equipment may include a high-pressure bulb tube. Before the CT scan images may be obtained by the CT equipment, a pre-treatment which may include an air calibration performed on the high-pressure bulb tube may be executed. One reason for performing air calibration may be that the performances of all channels of the detector in the CT equipment may not be exactly consistent, and thus the outputs of a pre-amplifier may not be entirely consistent even if intensities of X-ray incident to each channel of the detector are exactly consistent. Therefore, an air calibration procedure may be performed after the CT equipment is booted, and a set of air calibration data may be obtained and stored by scanning air, thereby using the set of air calibration data to correct the actual scan data when scanning the subject. In the following description, specific examples are used for describing the present disclosure in detail.

Figure 1:
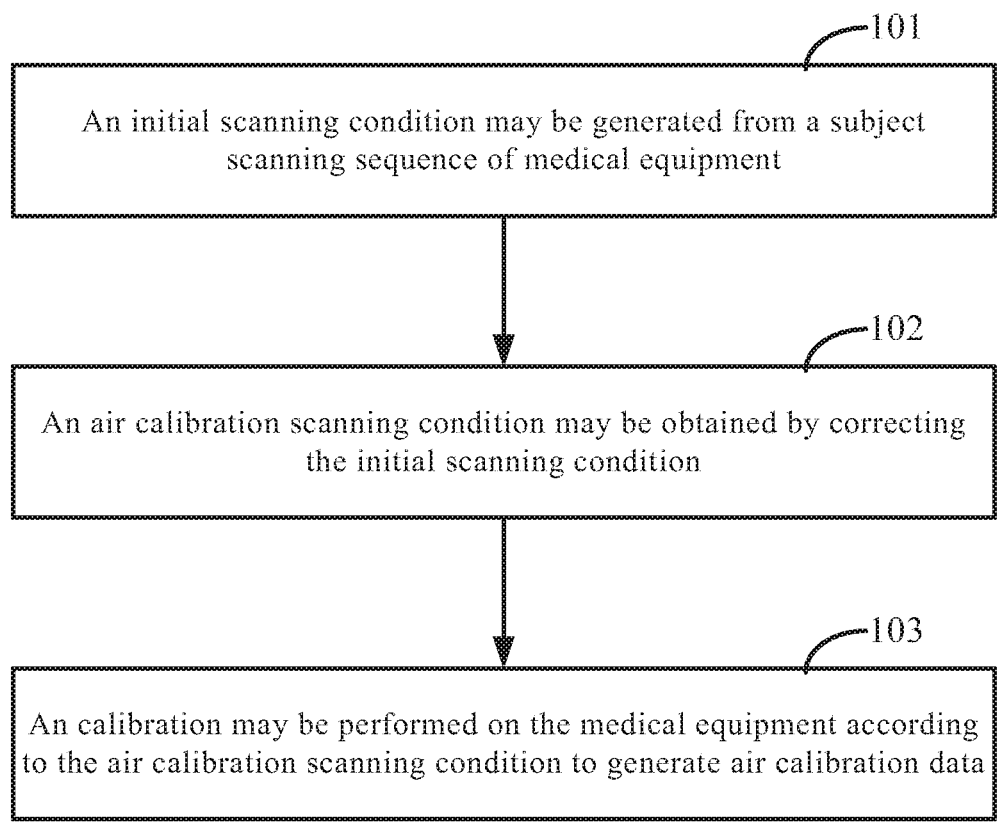
FIG. 1 is a flowchart illustrating the procedures of a method for air calibration according to an example of the present disclosure.

Referring to FIG. 1, this figure is a flowchart illustrating the procedures of a method for air calibration according to an example of the present disclosure.

At block 101, an initial scanning condition may be generated from a subject scanning sequence of medical equipment. The subject scanning sequence may be generated when a subject is scanned by the medical equipment to obtain an image of the subject and may be recorded in association with a subject ID uniquely identifying the subject.

When different subjects are scanned by the medical equipment to obtain subject images, the corresponding subject scanning sequence may be set in advance. The subject scanning sequence may include a plurality of scanning parameters, such as, a focus mode, a focus position, a focal spot size, a bulb tube voltage, a scanning resolution, a rotational speed, and/or a slice position or a combination thereof. Since the subject scanning sequence may be the scanning sequence actually used by the medical equipment during the clinical scanning process, the initial scanning condition may be firstly generated based on the subject scanning sequence in this example.

In an example, all recorded subject scanning sequences may be analyzed to generate the initial scanning condition. The specific operation is described below in the following description.

As one example, each time a subject may be scanned by the medical equipment, a subject ID may be assigned to the subject, and at least one subject scanning sequence may be used for the scanning of the subject. A correspondence relationship between the subject ID and the subject scanning sequence may be stored in the subject information database, wherein every subject ID may correspond to at least one subject scanning sequence. When performing an air calibration operation, the subject information database may be loaded by the medical equipment first. The subject information database, which may store one or more subject scanning sequences, may be filtered by deleting a subject scanning sequence in the subject information database which may comprise the same scanning parameter values as another subject scanning sequence in the subject information database. Comprising the same scanning parameter values may indicate that values of each scanning parameter in two subject scanning sequences may be the same. After loading the subject information database, an initial scanning condition table including one or more initial scanning conditions may be generated according to the filtered subject information database, wherein each of the initial scanning conditions may correspond to one subject scanning sequence in the filtered subject information database.

In another example, at the moment when the subject is being scanned, the subject scanning sequence in use may be analyzed to generate an initial scanning condition. The specific operation is described below in the following description.

Assume that a target subject scanning sequence may be used for scanning a target subject, and a plurality of historical subject scanning sequences may have been previously recorded in the subject information database before the target subject is scanned. Under this condition, the target subject scanning sequence may be compared with the recorded plurality of historical subject scanning sequences to determine whether the target subject scanning sequence comprises the same scanning parameter values as any one of the plurality of historical subject scanning sequences or not. If the target subject scanning sequence may not comprise the same scanning parameter values as any recorded historical subject scanning sequence, an initial scanning condition may be generated from the target subject scanning sequence and may be written into the initial scanning condition table. If the target subject scanning sequence comprises the same scanning parameter values as a recorded historical subject scanning sequence, the target subject scanning sequence may not be written into the initial scanning condition table. The initial scanning condition table may be directly used for performing air calibration.

At block 102, an air calibration scanning condition may be obtained by correcting the initial scanning condition.

A standardization process may be performed on scanning parameters of each initial scanning condition in an initial scanning condition table. The initial scanning condition table may be filtered by deleting a standardized initial scanning condition in the initial scanning condition table which may comprise the same scanning parameter values as another standardized initial scanning condition in the initial scanning condition table. After performing the standardization process, each of the standardized initial scanning conditions in the filtered initial scanning condition table may be written as the air calibration scanning condition into an air calibration scanning condition table.

After the scanning parameters of each initial scanning condition are read one by one, the value of a scanning parameter in the initial scanning condition may be compared with one or more parameter ranges corresponding to the scanning parameter defined in the air calibration scanning condition database, so as to determine a matched parameter range which may cover the value of the scanning parameter.

The value of the scanning parameter in the initial scanning condition may be rewritten with a standard value corresponding to the matched parameter range defined in the air calibration scanning condition database. For example, the scanning parameter may be a rotational speed, wherein the rotational speed may usually be characterized by a rotation time that a gantry takes to rotate the equipment in a 360-degree circle. In an example, assume that a correspondence relationship between the parameter range and the standard parameter in the air calibration scanning condition database is that: when the range of the rotational speed is between 0 s and 0.8 s, the corresponding standard parameter of the rotational speed may be 0.6 s; and when the range of the rotational speed is between 0.8 s and 1 s, the corresponding standard parameter of the rotational speed may be 1 s. For example, if the read rotational speed is 0.5 s, which is between 0 s and 0.8 s, the corresponding standardized rotational speed may be 0.6 s; if the read rotational speed is 0.7 s, the corresponding standardized rotational speed may be 0.6 s; and if the read rotational speed is 0.9 s, the corresponding standardized rotational speed may be 1 s.

At block 103, an air calibration may be performed on the medical equipment according to the air calibration scanning condition to generate air calibration data.

After the air calibration scanning condition may be obtained, scanning parameters of the medical equipment may then be set according to the scanning parameters contained in the air calibration scanning condition. The medical equipment may scan air according to the set scanning parameters to thereby generate air calibration data under the air calibration scanning condition.

As may be seen from the abovementioned example, the initial scanning condition may be generated from the subject scanning sequence of the medical equipment, and the air calibration scanning condition may be obtained by correcting the initial scanning condition. For various medical institutions, the air calibration scanning sequences obtained based on the actual subject scanning sequence of the medical equipment may ensure that the air calibration scanning conditions are common, and a number of air calibration scanning conditions may be reduced, thereby also reducing a number of air calibration procedures performed by the medical equipment and lowering loss of the high-pressure bulb tube which may extend the life time of the medical equipment.

Figure 2:
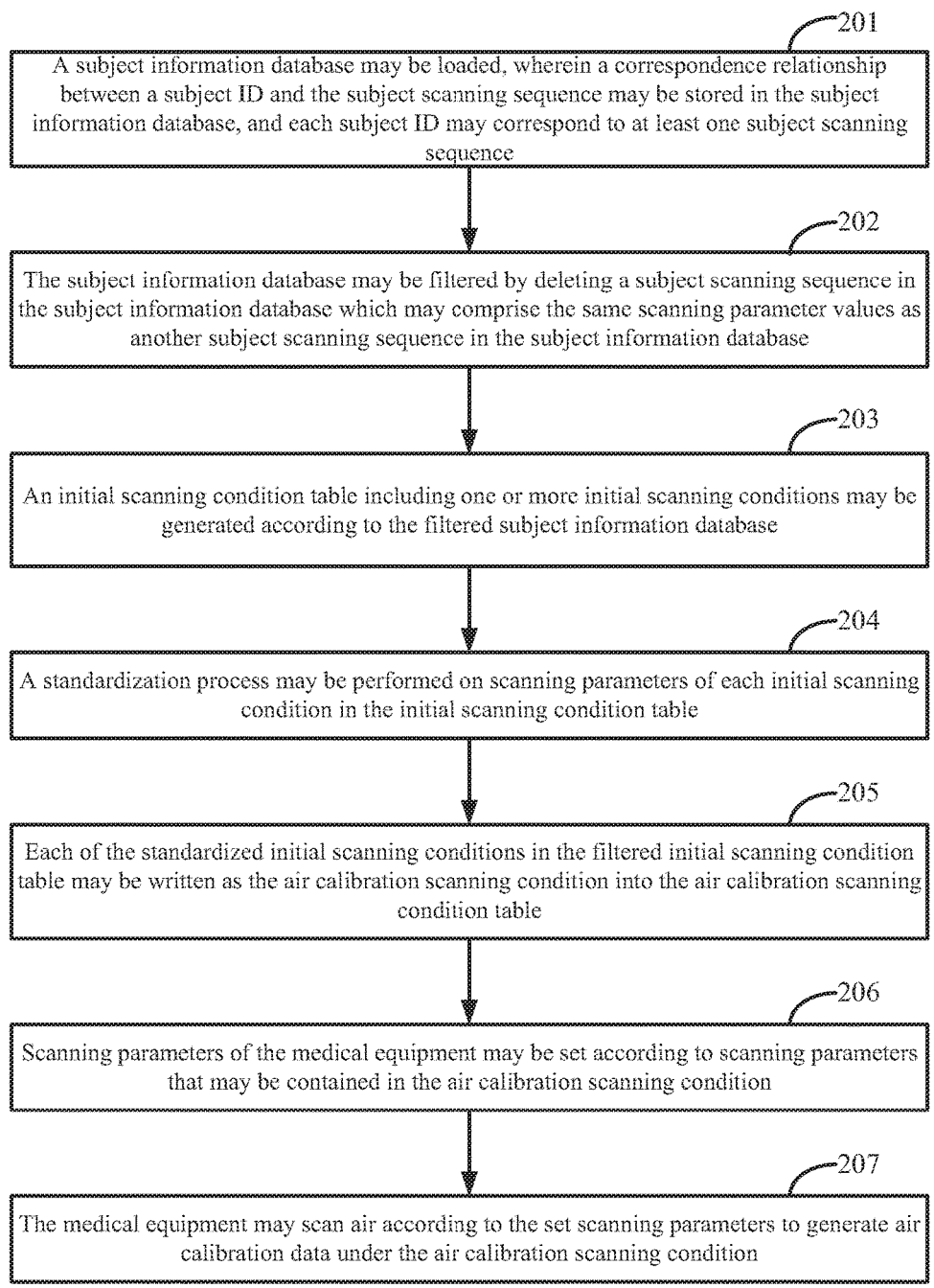
FIG. 2 is a flowchart illustrating the procedures of a method for air calibration according to another example of the present disclosure.

Referring to FIG. 2, this figure is a flowchart illustrating the procedures of a method for air calibration according to another example of the present disclosure. In this example, the procedures for obtaining the air calibration scanning condition by loading a subject information database so as to perform the air calibration are described in detail.

At block 201, a subject information database may be loaded, wherein a correspondence relationship between a subject ID and the subject scanning sequence may be stored in the subject information database, and each subject ID may correspond to at least one subject scanning sequence.

In this example, each time the subject may be scanned by the medical equipment, one subject ID may be assigned to the subject, and at least one subject scanning sequence may be used for scanning the subject. A correspondence relationship between the subject ID and the subject scanning sequence may be stored in the subject information database, wherein each subject ID may correspond to at least one subject scanning sequence.

Before performing air calibration, the subject information database may be loaded by the medical equipment first. An example of the subject information database is shown in the following Table 1.

TABLE 1

| Subject ID | Subject Scanning Sequence | | |
|---|---|---|---|
| ID-1 | Scan-1 | Scan-2 | |
| ID-2 | Scan-1 | | |
| ID-3 | Scan-1 | Scan-2 | Scan-3 |
| ID-4 | Scan-1 | ... | Scan-6 |
| ID-5 | Scan-1 | Scan-2 | ... |

According to Table 1 for example, the subject ID is indicated by ID-1, and the subject ID "ID-1" may correspond to two subject scanning sequences Scan-1 and Scan-2. This may mean that the subject ID-1 may have been scanned by using these two subject scanning sequence Scan-1 and Scan-2 during the actual clinical scanning process. According to Table 1 above, each subject scanning sequence may contain a plurality of scanning parameters. These scanning parameters are not shown in Table 1. The scanning parameters may include a focus mode, a focus position, a focal spot size, a bulb tube voltage, a scanning resolution, a rotational speed, and/or a slice position, etc.

At block 202, the subject information database may be filtered by deleting a subject scanning sequence in the subject information database which may comprise the same scanning parameter values as another subject scanning sequence in the subject information database, wherein having the same scanning parameter values may indicate that values of each scanning parameter in two subject scanning sequences may be the same.

After the subject information database is loaded at block 201, a subject scanning sequence table as shown in Table 2 below may be obtained.

By combining Table 2 above, the values of scanning parameters of all of the subject scanning sequences shown in Table 2 may be traversed so as to filter the subject scanning sequences comprising the same scanning parameter values. For example, as shown in Table 2, the values of scanning parameters contained in the subject scanning sequence ID-1 (Scan-1) and the subject scanning sequence ID-1 (Scan-2) may be the same and thus, any one of these two subject scanning sequence may be filtered.

At block 203, an initial scanning condition table including one or more initial scanning conditions may be generated according to the filtered subject information database, wherein each of the initial scanning conditions may correspond to one subject scanning sequence in the filtered subject information database.

After the subject scanning sequence table shown in Table 2 is filtered at block 202, an initial scanning condition table including one or more initial scanning conditions may be generated according to the filtering result. Each of the initial scanning conditions may correspond to one subject scanning sequence in the filtered subject scanning sequence table, which is shown in an example in Table 3.

TABLE 3

| Initial Scanning Condition | Focus Mode | Focus Position | Focal Spot Size | Bulb Tube Voltage | Scanning Resolution | Rotational Speed | Slice Position |
|---|---|---|---|---|---|---|---|
| Condition-1 | 2 | 2 | 1 | 80 | 0 | 1 | 2*0.625 |
| Condition-2 | 8 | 0 | 0 | 80 | 1 | 0.6 | 16*0.625 |
| Condition-3 | 216 | 0 | 1 | 100 | 0 | 1 | 8*0.625 |
| Condition-4 | 8 | 0 | 0 | 80 | 1 | 0.5 | 16*0.625 |
| ... | ... | ... | ... | ... | ... | ... | ... |

At block 204, a standardization process may be performed on scanning parameters of each initial scanning condition in the initial scanning condition table.

After the scanning parameters of each initial scanning condition may be read one by one, the value of a scanning parameter in the initial scanning condition may be compared with one or more parameter ranges corresponding to the scanning parameter defined in an air calibration scanning condition database, so as to determine a matched parameter range which may cover the value of the scanning parameter. The value of the scanning parameter in the initial scanning condition may be rewritten with a standard value corresponding to the matched parameter range defined in the air calibration scanning condition database.

For example, a correspondence relationship between the parameter range of the rotational speed and the standard

TABLE 2

| Subject Scanning Sequence | Focus Mode | Focus Position | Focal Spot Size | Bulb Tube Voltage | Scanning Resolution | Rotational Speed | Slice Position |
|---|---|---|---|---|---|---|---|
| ID-1 (Scan-1) | 2 | 2 | 1 | 80 | 0 | 1 | 2*0.625 |
| ID-1 (Scan-2) | 2 | 2 | 1 | 80 | 0 | 1 | 2*0.625 |
| ID-2 (Scan-1) | 8 | 0 | 0 | 80 | 1 | 0.6 | 16*0.625 |
| ID-3 (Scan-1) | 216 | 0 | 1 | 100 | 0 | 1 | 8*0.625 |
| ID-3 (Scan-2) | 8 | 0 | 0 | 80 | 1 | 0.5 | 16*0.625 |
| ... | ... | ... | ... | ... | ... | ... | ... | parameter defined in the air calibration scanning condition database may be that: when the parameter range of the rotational speed is between 0 s and 0.8 s, the corresponding standard parameter of the rotational speed may be 0.6 s; and when the parameter range of the rotational speed is between 0.8 s and 1 s, the corresponding standard parameter of the rotational speed may be 1 s. Based on the abovementioned example, a standardized initial scanning condition table shown in Table 4 may be obtained by performing a standardization process on the rotational speed in the initial scanning condition table at block 203.

TABLE 4

| Standardized Initial Scanning Condition | Focus Mode | Focus Position | Focal Spot Size | Bulb Tube Voltage | Scanning Resolution | Rotational Speed | Slice Position |
|---|---|---|---|---|---|---|---|
| StdCondition-1 | 2 | 2 | 1 | 80 | 0 | 1 | 2*0.625 |
| StdCondition-2 | 8 | 0 | 0 | 80 | 1 | 0.6 | 16*0.625 |
| StdCondition-3 | 216 | 0 | 1 | 100 | 0 | 1 | 8*0.625 |
| StdCondition-4 | 8 | 0 | 0 | 80 | 1 | 0.6 | 16*0.625 |
| ... | ... | ... | ... | ... | ... | ... | ... |

At block 205, each of the standardized initial scanning conditions in the filtered initial scanning condition table may be used as the air calibration scanning condition, and may be written into the air calibration scanning condition table.

Based on Table 4, and as shown in the block 204, any one of the Standardized Initial Scanning Conditions, StdCondition-2 and StdCondition-4 having the same scanning parameter values, may be filtered so as to generate an air calibration scanning condition table, which is shown in an example in Table 5 below.

TABLE 5

| Air Calibration Scanning Condition | Focus Mode | Focus Position | Focal Spot Size | Bulb Tube Voltage | Scanning Resolution | Rotational Speed | Slice Position |
|---|---|---|---|---|---|---|---|
| AirCondition-1 | 2 | 2 | 1 | 80 | 0 | 1 | 2*0.625 |
| AirCondition-2 | 8 | 0 | 0 | 80 | 1 | 0.6 | 16*0.625 |
| AirCondition-3 | 216 | 0 | 1 | 100 | 0 | 1 | 8*0.625 |
| ... | ... | ... | ... | ... | ... | ... | ... |

At block 206, scanning parameters of the medical equipment may be set according to scanning parameters that may be contained in the air calibration scanning condition.

At block 207, the medical equipment may scan air according to the set scanning parameters to generate air calibration data under the air calibration scanning condition.

After obtaining the air calibration scanning condition, the abovementioned blocks 206 and 207 which may be used for performing the air calibration based on the air calibration scanning condition, may be consistent with the existing air calibration process.

As can be seen from the example provided above, the initial scanning condition may be generated according to the subject scanning sequence of the medical equipment, and the initial scanning condition may be corrected so as to obtain the air calibration scanning condition. For various medical institutions, the air calibration scanning sequences obtained based on the actual subject scanning sequence of the medical equipment may ensure that the air calibration scanning conditions are common, and a number of air calibration scanning conditions may be reduced, thereby also reducing a number of air calibration procedures performed by the medical equipment and potentially lowering loss of the high-pressure bulb tube to extend the life time of the medical equipment.

In accordance with the method for air calibration of the present disclosure, medical equipment equipped with an air calibration device may be further provided in the present disclosure.

Figure 3:
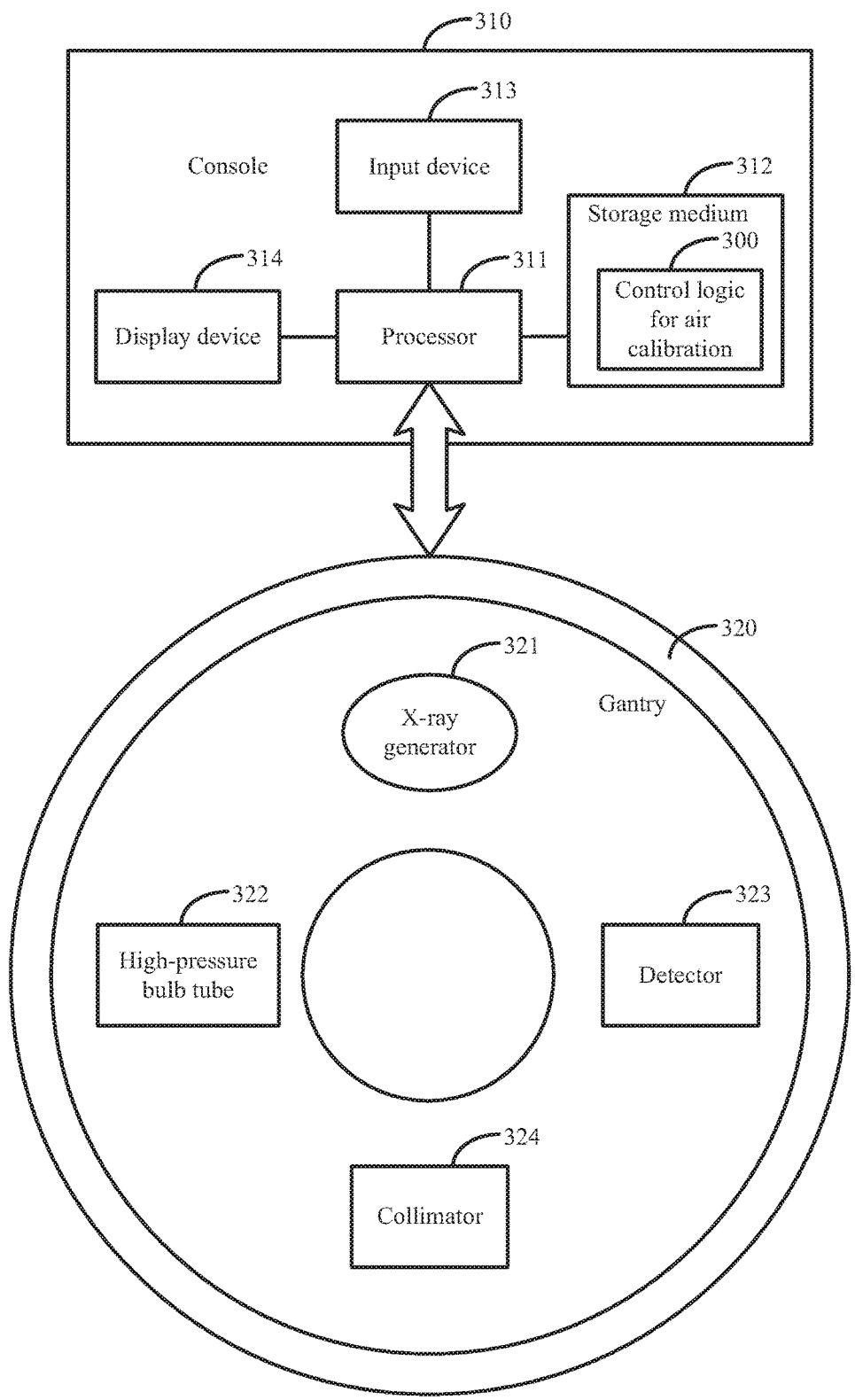
FIG. 3 is system architecture diagram of a medical equipment equipped with a device for air calibration according to an example of the present disclosure.

Shown in FIG. 3 is system architecture diagram of medical equipment which may be equipped with an air calibration device according to an example of the present disclosure. Take CT equipment as an example, the medical equipment may include a console 310 and a gantry 320. The console 310 may include a processor 311, a storage medium 312, an input device 313, and a display device 314, etc. The gantry 320 may include an X-ray generator 321, a high-pressure bulb tube 322, a detector 323, and a collimator 324, etc. The storage medium 312 may be used for storing machine readable instructions corresponding to a control logic for air calibration 300. In different examples, the storage medium 312 may be Read Only Memory (ROM), volatile memory, non-volatile memory, flash memory, storage drives (such as, a hard drive), solid state drive, any type of storage disks (such as, CD-ROM, DVD, etc.), or similar storage medium, or a combination thereof.

If the air calibration may be required, the processor 311 may read the machine readable instructions corresponding to the control logic for air calibration 300 from the storage medium 312. In an example, if the air calibration may be required, the processor 311 may read and execute machine readable instructions stored in the storage medium 312 to:

generate an initial scanning condition from a subject scanning sequence of the medical equipment, wherein, the subject scanning sequence may be generated when a subject is scanned by the medical equipment to obtain an image of the subject and may be recorded in association with a subject ID uniquely identifying the subject;

obtain an air calibration scanning condition by correcting the initial scanning condition; and perform an air calibration on the medical equipment according to the air calibration scanning condition to generate air calibration data.

In an example, the processor 311 executing machine readable instructions of the control logic for air calibration 300 stored in the storage medium 312 to generate an initial scanning condition from a subject scanning sequence of a medical equipment may cause the processor 311 to:

load a subject information database which may store one or more subject scanning sequences;

filter the subject information database by deleting a subject scanning sequence in the subject information database which may comprise the same scanning parameter values as another subject scanning sequence in the subject information database, wherein comprising the same scanning parameter values may indicate that values of each scanning parameter in two subject scanning sequences may be the same; and generate an initial scanning condition table including one or more initial scanning conditions according to the filtered subject information database, wherein each of the initial scanning conditions may correspond to one subject scanning sequence in the filtered subject information database.

In an example, the processor 311 executing machine readable instructions of the control logic for air calibration 300 stored in the storage medium 312 to generate an initial scanning condition from a subject scanning sequence of the medical equipment may cause the processor 311 to:

determine whether a target subject scanning sequence comprises the same scanning parameter values as a subject scanning sequence recorded in the subject information database when the target subject scanning sequence may be or is being performed by the medical equipment; and generate an initial scanning condition from the target subject scanning sequence and write the generated initial scanning condition into the initial scanning condition table if the determination result is no.

In an example, the processor 311 executing machine readable instructions of the control logic for air calibration 300 stored in the storage medium 312 to obtain an air calibration scanning condition by correcting the initial scanning condition may cause the processor 311 to:

perform a standardization process of scanning parameters of each initial scanning condition in the initial scanning condition table;

filter the initial scanning condition table by deleting a standardized initial scanning condition in the initial scanning condition table which may comprise the same scanning parameter values as another standardized initial scanning condition in the initial scanning condition table, wherein having the same scanning parameter values may indicate that values of each scanning parameter in two initial scanning conditions may be the same;

write each of the standardized initial scanning conditions in the filtered initial scanning condition table as an air calibration scanning condition into an air calibration scanning condition table.

In an example, the processor 311 executing machine readable instructions of the control logic for air calibration 300 stored in the storage medium 312 to perform a standardization process on scanning parameters of each initial scanning condition in the initial scanning condition table may cause the processor 311 to:

compare the value of a scanning parameter in the initial scanning condition with one or more parameter ranges corresponding to the scanning parameter defined in an air calibration scanning condition database, so as to determine a matched parameter range which may cover the value of the scanning parameter; and rewrite the value of the scanning parameter in the initial scanning condition with a standard value corresponding to the matched parameter range defined in the air calibration scanning condition database.

In an example, the processor 311 executing machine readable instructions of the control logic for air calibration 300 stored in the storage medium 312 to perform an air calibration on the medical equipment according to the air calibration scanning condition to generate air calibration data may cause the processor 311 to:

set scanning parameters of the medical equipment according to scanning parameters contained in the air calibration scanning condition; and cause the medical equipment to scan air according to the set scanning parameters, so as to generate air calibration data under the air calibration scanning conditions.

Figure 4:
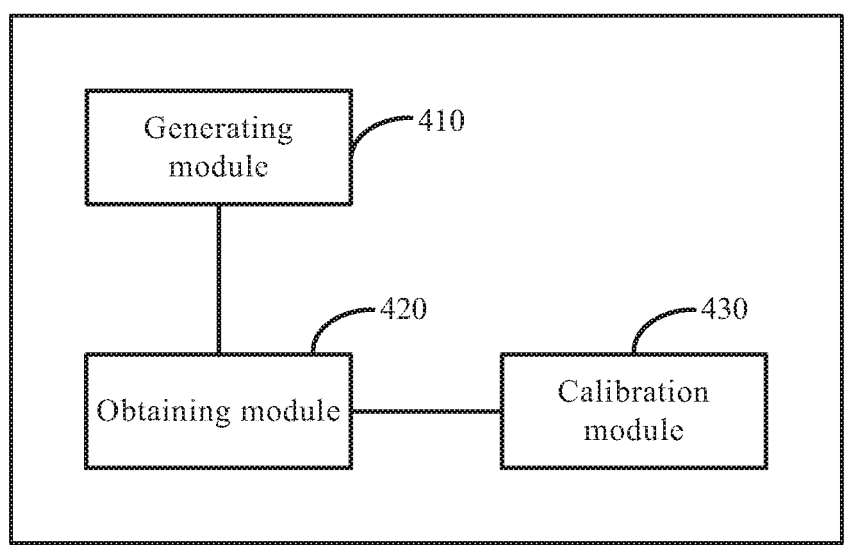
FIG. 4 is a block diagram of an example control logic for air calibration according to an example of the present disclosure.

The storage medium 312 may store machine readable instructions corresponding to an example control logic for air calibration 300. Referring to FIG. 4, this figure is a block diagram of an example control logic for air calibration according to an example of the present disclosure. As shown in FIG. 4, the control logic for air calibration may include a generating module 410, an obtaining module 420, and a calibration module 430.

The generating module 410 may be used for generating an initial scanning condition from a subject scanning sequence of medical equipment, wherein the subject scanning sequence may be generated when a subject is scanned by the medical equipment in order to obtain an image of the subject. The scanning sequence may then be recorded in association with a subject ID uniquely identifying the subject.

The obtaining module 420 may be used for obtaining an air calibration scanning condition by correcting the initial scanning condition.

The calibration module 430 may be used for performing an air calibration on the medical equipment according to the air calibration scanning condition to generate air calibration data.

In an alternative implementation, the generating module 410 may further include (not shown in FIG. 4): a data loading sub-module, a sequence filtering sub-module, and a sequence generating sub-module.

The data loading sub-module may be used for loading a subject information database which may store one or more subject scanning sequences.

The sequence filtering sub-module may be used for filtering the subject information database by deleting a subject scanning sequence in the subject information database which may comprise the same scanning parameter values as another subject scanning sequence in the subject information database, wherein having the same scanning parameter values may indicate that values of each scanning parameter in two subject scanning sequences may be the same.

The sequence generating sub-module may be used for generating an initial scanning condition table including one or more initial scanning conditions according to the filtered subject information database, wherein each of the initial scanning conditions may correspond to one subject scanning sequence in the filtered subject information database.

In another alternative implementation, the generating module 410 may further include (not shown in FIG. 4): a sequence determining sub-module and a determination executing sub-module.

The sequence determining sub-module may be used for determining whether a target subject scanning sequence comprising the same scanning parameter values as a subject scanning sequence recorded in the subject information database when the target subject scanning sequence may be or is being performed by the medical equipment.

The determination executing sub-module may be used for generating an initial scanning condition from the target subject scanning sequence and writing the generated initial scanning condition into the initial scanning condition table if the determination result is no.

In another alternative implementation, the obtaining module 420 may further include (not shown in FIG. 4): a standardization sub-module and a scanning condition generating sub-module.

The standardization sub-module may be used for performing a standardization process on scanning parameters of each initial scanning condition in the initial scanning condition table. The standardization sub-module may also be used for filtering the initial scanning condition table by deleting a standardized initial scanning condition in the initial scanning condition table which comprises the same scanning parameter values as another standardized initial scanning condition in the initial scanning condition table, wherein having the same scanning parameter values may indicate that values of each scanning parameter in two initial scanning condition may be the same.

The scanning condition generating sub-module may be used for writing each of the standardized initial scanning conditions in the filtered initial scanning condition table as an air calibration scanning condition into an air calibration scanning condition table.

In an example, the standardization sub-module may be implemented by: comparing the value of a scanning parameter in the initial scanning condition with one or more parameter ranges corresponding to the scanning parameter defined in an air calibration scanning condition database, so as to determine a matched parameter range which may cover the value of the scanning parameter; and rewriting the value of the scanning parameter in the initial scanning condition with a standard value corresponding to the matched parameter range defined in the air calibration scanning condition database.

In another alternative implementation, the calibration module 430 may further include (not shown in FIG. 4): a parameter setting sub-module and a calibration performing sub-module.

The parameter setting sub-module may be used for setting scanning parameters of the medical equipment according to scanning parameters contained in the air calibration scanning condition.

The calibration performing sub-module may be used for causing the medical equipment to scan air according to the set scanning parameters, so as to generate air calibration data under the air calibration scanning conditions.

In another alternative implementation, the air calibration scanning condition may include a combination of a plurality of scanning parameters; and the plurality of scanning parameters may include any one or more of a focus mode, a focus position, a focal spot size, a bulb tube voltage, a scanning resolution, a rotational speed, and a slice position.

The functions and their implementations of the above modules may refer to the steps of the above-described method for air calibration, and their detailed description may be omitted here.

The above are only preferred examples of the present disclosure is not intended to limit the disclosure within the spirit and principles of the present disclosure, any changes made, equivalent replacement, or improvement in the protection of the present disclosure should be contained within the range of the present disclosure.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product may be stored in a storage medium and may comprise a plurality of instructions for making a processor to implement the methods recited in the examples of the present disclosure.

The figures are only illustrations of an example, wherein the units or procedure shown in the figures may not necessarily be essential for implementing the present disclosure. Those skilled in the art will understand that the units in the device in the example may be arranged in the device in the examples as described, or may be alternatively located in one or more devices different from that in the examples. The units in the examples described may be combined into one module or may be further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for air calibration, the method comprising:
generating an initial scanning condition from a subject scanning sequence of a medical equipment, wherein the subject scanning sequence is generated when a subject is scanned by the medical equipment to obtain an image of the subject and is recorded in association with a subject ID uniquely identifying the subject;
obtaining an air calibration scanning condition by correcting the initial scanning condition; and
generating air calibration data by performing an air calibration on the medical equipment with the air calibration scanning condition;
wherein generating the initial scanning condition from the subject scanning sequence of a medical equipment comprises:
loading a subject information database which stores one or more subject scanning sequences;
filtering the subject information database by deleting a subject scanning sequence in the subject information database which has the same scanning parameter values as another subject scanning sequence in the subject information database, wherein having the same scanning parameter values indicates values of each scanning parameter in two subject scanning sequences are the same; and generating an initial scanning condition table including one or more initial scanning conditions according to the filtered subject information database, wherein each of the initial scanning conditions corresponds to one subject scanning sequence in the filtered subject information database.

2. The method according to claim 1, wherein said generating an initial scanning condition from a subject scanning sequence of a medical equipment comprises:

determining whether a target subject scanning sequence has the same scanning parameter values as a subject scanning sequence recorded in the subject information database when the target subject scanning sequence is to be or being performed by the medical equipment; and generating an initial scanning condition from the target subject scanning sequence and writing the generated initial scanning condition into the initial scanning condition table if the determination result is no.

3. The method according to claim 1, wherein said obtaining an air calibration scanning condition by correcting the initial scanning condition comprises:

performing a standardization process on scanning parameters of each initial scanning condition in the initial scanning condition table; and filtering the initial scanning condition table by deleting a standardized initial scanning condition in the initial scanning condition table which has the same scanning parameter values as another standardized initial scanning condition in the initial scanning condition table, wherein having the same scanning parameter values indicates values of each scanning parameter in two initial scanning conditions are the same;

writing each of the standardized initial scanning conditions in the filtered initial scanning condition table as an air calibration scanning condition into an air calibration scanning condition table.

4. The method according to claim 3, wherein said performing a standardization process on scanning parameters of each initial scanning condition in the initial scanning condition table comprises:

comparing the value of a scanning parameter in the initial scanning condition with one or more parameter ranges corresponding to the scanning parameter defined in an air calibration scanning condition database, so as to determine a matched parameter range which covers the value of the scanning parameter; and rewriting the value of the scanning parameter in the initial scanning condition with a standard value corresponding to the matched parameter range defined in the air calibration scanning condition database.

5. The method according to claim 1, wherein said generating air calibration data by performing an air calibration on the medical equipment with the air calibration scanning condition comprises:

setting scanning parameters of the medical equipment according to scanning parameters contained in the air calibration scanning condition; and causing the medical equipment to scan air according to the set scanning parameters, so as to generate air calibration data under the air calibration scanning condition.

6. The method according to claim 1, wherein
the air calibration scanning condition comprises a combination of a plurality of scanning parameters; and
the plurality of scanning parameters comprises any one or more of a focus mode, a focus position, a focal spot size, a bulb tube voltage, a scanning resolution, a rotational speed, and a slice position.

7. An air calibration device comprising:
a processor which invokes machine readable instructions corresponding to a control logic for air calibration stored on a storage medium and executes the machine readable instructions to:

generate an initial scanning condition from a subject scanning sequence of a medical equipment, wherein the subject scanning sequence is generated when a subject is scanned by the medical equipment to obtain an image of the subject and is recorded in association with a subject ID uniquely identifying the subject;

obtain an air calibration scanning condition by correcting the initial scanning condition; and generate air calibration data by performing an air calibration on the medical equipment with the air calibration scanning condition;

wherein, when generating an initial scanning condition from a subject scanning sequence of a medical equipment, the machine readable instructions further cause the processor to:

load a subject information database which stores one or more subject scanning sequences;

filter the subject information database by deleting a subject scanning sequence in the subject information database which has the same scanning parameter values as another subject scanning sequence in the subject information database, wherein having the same scanning parameter values indicates values of each scanning parameter in two subject scanning sequences are the same; and generate an initial scanning condition table including one or more initial scanning conditions according to the filtered subject information database, wherein each of the initial scanning conditions corresponds to one subject scanning sequence in the filtered subject information database.

8. The device according to claim 7, wherein said machine readable instructions further cause the processor to:

determine whether a target subject scanning sequence has the same scanning parameter values as a subject scanning sequence recorded in the subject information database when the target subject scanning sequence is to be or being performed by the medical equipment; and generate an initial scanning condition from the target subject scanning sequence and write the generated initial scanning condition into the initial scanning condition table if the determination result is no.

9. The device according to claim 7, wherein said machine readable instructions further cause the processor to:

perform a standardization process on scanning parameters of each initial scanning condition in the initial scanning condition table; and filter the initial scanning condition table by deleting a standardized initial scanning condition in the initial scanning condition table which has the same scanning parameter values as another standardized initial scanning condition in the initial scanning condition table, wherein having the same scanning parameter values indicates values of each scanning parameter in two initial scanning conditions are the same;

write each of the standardized initial scanning conditions in the filtered initial scanning condition table as an air calibration scanning condition into an air calibration scanning condition table.

10. The device according to claim 9, wherein said machine readable instructions further cause the processor to:

compare the value of a scanning parameter in the initial scanning conditions with one or more parameter ranges corresponding to the scanning parameter defined in an air calibration scanning condition database, so as to determine a matched parameter range which covers the value of the scanning parameter; and rewrite the value of the scanning parameter in the initial scanning condition with a standard value corresponding to the matched parameter range defined in the air calibration scanning condition database.

11. The device according to claim 7, wherein said machine readable instructions further cause the processor to:

set scanning parameters of the medical equipment according to scanning parameters contained in the air calibration scanning condition; and cause the medical equipment to scan air according to the set scanning parameters, so as to generate air calibration data under the air calibration scanning condition.

12. The device according to claim 7, wherein the air calibration scanning condition comprises a combination of a plurality of scanning parameters; and the plurality of scanning parameters comprises any one or more of a focus mode, a focus position, a focal spot size, a bulb tube voltage, a scanning resolution, a rotational speed, and a slice position.

13. A non-transitory computer readable storage medium storing instructions executable by a processor and upon such execution causes the processor to:

generate an initial scanning condition from a subject scanning sequence of a medical equipment, wherein the subject scanning sequence is generated when a subject is scanned by the medical equipment to obtain an image of the subject and is recorded in association with a subject ID uniquely identifying the subject;

obtain an air calibration scanning condition by correcting the initial scanning condition; and generate air calibration data by performing an air calibration on the medical equipment with the air calibration scanning condition;

wherein, when generating an initial scanning condition from a subject scanning sequence of a medical equipment, the instructions cause the processor to:

load a subject information database which stores one or more subject scanning sequences;

filter the subject information database by deleting a subject scanning sequence in the subject information database which has the same scanning parameter values as another subject scanning sequence in the subject information database, wherein having the same scanning parameter values indicates values of each scanning parameter in two subject scanning sequences are the same; and generate an initial scanning condition table including one or more initial scanning conditions according to the filtered subject information database, wherein each of the initial scanning conditions corresponds to one subject scanning sequence in the filtered subject information database.

* * * * *